United States Patent [19]
Cook

[11] Patent Number: 5,162,341
[45] Date of Patent: Nov. 10, 1992

[54] USE OF SIGMA RECEPTOR ANTAGONISTS FOR TREATMENT OF AMPHETAMINE ABUSE

[75] Inventor: Leonard Cook, Newark, Del.

[73] Assignee: Du Pont Merck Pharmaceutical Company, Wilmington, Del.

[21] Appl. No.: 659,443

[22] Filed: Feb. 22, 1991

[51] Int. Cl.$^5$ ............... A61K 31/445; A61K 31/505; A61K 31/44; A61K 31/40

[52] U.S. Cl. .................... 514/317; 514/256; 514/306; 514/314; 514/318; 514/323; 514/326; 514/415; 514/419

[58] Field of Search ............... 514/332, 256, 306, 314, 514/317, 318, 323, 326, 415, 419

[56] References Cited

PUBLICATIONS

Schlemmer et al., Soc. Neurosci. Abstr. 12(1):480 (1986).
Taylor et al., Drug Development Research 11:65–70 (1987).
Snyder et al., J. Neuropsychiatry 1:7–15 (1989).
Hock et al., Drug Development Research 6:301–311 (1985).
Ferris et al., Life Sciences 38:2329–2337 (1986).
Ogren et al., Eur. J. Pharmacology 102:459–474 (1984).

Primary Examiner—Frederick E. Waddell
Assistant Examiner—Diane Gardner
Attorney, Agent, or Firm—Blair Q. Ferguson

[57] ABSTRACT

The invention relates to a method of treating drug abuse or addiction involving amphetamine or amphetamine-related drugs with pharmacological effects similar to amphetamine in a mammal which comprises administering to the mammal an effective amount, to reduce the pharmacological effects of the amphetamine or amphetamine-related drug, of certain piperidine sigma receptor antagonists.

23 Claims, 1 Drawing Sheet

USE OF SIGMA RECEPTOR ANTAGONISTS FOR TREATMENT OF AMPHETAMINE ABUSE

BACKGROUND OF THE INVENTION

There is presently a need for methods of treatment for drug abuse involving such drugs as amphetamine and amphetamine-related drugs exhibiting similar pharmacological effects as amphetamine.

Amphetamines in large doses cause psychotomimetic effects that resemble acute paranoid schizophrenia and are relieved by neuroleptics, which are the primary antipsychotic drugs used in the treatment of schizophrenia (Snyder and Largent (1989) J. Neuropsychiatry 1: 7-15). The neuroleptics cinuperone (HR375), chlorpromazine, haloperidol, and clozapine have been reported to antagonize the effects of amphetamine in animals (Hock et al. (1985) Drug Development Research 6: 301-311). Some neuroleptics, such as tiospirone, haloperidol, and cinuperone, exhibit high affinity and non-selective binding to both sigma receptors and dopamine $D_2$ receptors (Snyder and Largent (1989) J. Neuropsychiatry 1: 7-15). Since the behavioral effects of amphetamines derive primarily from the synaptic release of dopamine, it is believed that the antagonism of the effects of amphetamine by neuroleptics is mediated by antagonism of the dopamine receptor system by neuroleptics.

The antipsychotic BMY14802, which exhibits relatively selective binding to sigma receptors relative to dopamine $D_2$ receptors, has been reported to antagonize amphetamine-induced behavioral changes considered to be relevant to psychosis (Schlemmer and Davis (1986) Soc. Neurosci. Abstr. 12: 480).

SUMMARY OF THE INVENTION

In the present invention, certain piperidine sigma receptor antagonists, lacking or having relatively weak dopamine receptor-blocking activity, were discovered to reduce and counteract the pharmacological effects of amphetamine in a mammal. By "sigma receptor antagonists lacking or having relatively weak dopamine receptor-blocking activity" we mean compounds having an inhibition constant, $K_i$, for sigma receptors of less than 500 nM and having at least a 5-fold greater affinity for sigma receptors than for dopamine receptors. The sigma receptor antagonists useful in the present invention preferably have a $K_i$ for sigma receptors of less than 100 nM and have at least a 50 to 100-fold greater affinity for sigma receptors than for dopamine receptors.

Unlike neuroleptics, the sigma receptor antagonists useful in the method of the present invention are selective for the sigma receptor and lack or have relatively weak dopamine receptor blocking activity. Thus, the selective sigma antagonists useful in the present invention, unlike neuroleptics, elicit their effects without directly antagonizing the dopamine receptor system.

The sigma receptor antagonists useful in the present invention have weak affinity for dopamine receptors relative to their affinity for sigma receptors. We have discovered that such selective sigma receptor antagonists are able to selectively antagonize the effects of amphetamine in an animal. In mouse animal models, it was found that a representative sigma receptor antagonist having weak dopamine receptor-blocking activity selectively antagonized the amphetamine-induced behavior (amphetamine-increased motor activity) without any significant depression in the normal baseline motor activity in animals in the absence of amphetamine. This important and unexpected finding suggests that sigma receptor antagonists having weak dopamine receptor-blocking activity will effectively antagonize and attenuate the pharmacological effects of amphetamine in humans at doses which will not have significant undesirable neurotoxic or adverse neurological effects.

The selective antagonism and attenuation of the pharmacological effects of amphetamine by sigma receptor antagonists having weak dopamine receptor-blocking activity contrasts with the effect of dopamine receptor-blocking neuroleptics, such as haloperidol. Haloperidol causes an adverse non-selective attenuation of normal motor activity in amphetamine-free animals at the same concentrations required to inhibit amphetamine-induced motor activity. Thus, the sigma receptor antagonists having weak dopamine receptor-blocking activity show a substantial and unexpected advantage over dopamine receptor-blocking neuroleptics in the treatment of amphetamine abuse.

The present invention provides a method of treating drug abuse or addiction in a mammal, involving amphetamine or amphetamine-related drugs exhibiting similar pharmacological effects as amphetamine, by administering to the mammal an effective amount of certain sigma receptor antagonists lacking or having relatively weak dopamine receptor-blocking activity. Amphetamine-related drugs, the effects of which are treated by the method of the present invention, include methamphetamine, 3,4-methylenedioxy-amphetamine (MDA), 3,4-methylenedioxy-methamphetamine (MDMA; "ecstasy") and other related "designer drugs".

The sigma receptor antagonist compounds useful in this invention include (N-phthalimidoalkyl) piperidines of the formula:

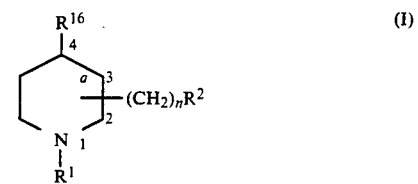

or a pharmaceutically acceptable salt or an N-oxide thereon wherein:

a is a single or double bond, provided that when a is a double bond then $R^2(CH_2)_n$ is attached at C-4;

n is 0-4, provided that when $(CH_2)_nR^2$ is attached to the 2-position of the piperidine ring then n is 2-4;

$R^1$ is $(CH_2)_mR^3$ or $(CH_2)_pAr$, where m is 1-4 and p is 1-4;

$R^2$ is

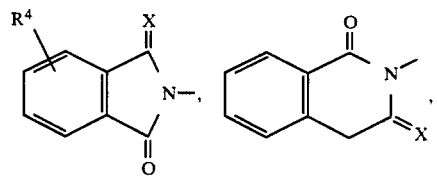

-continued
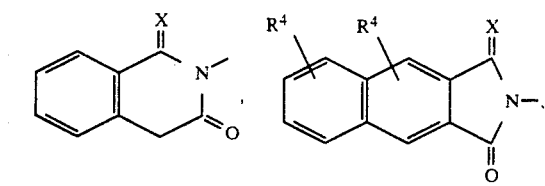
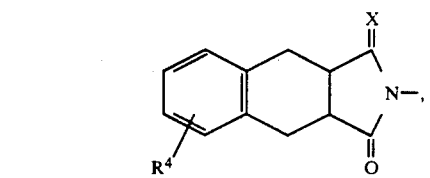
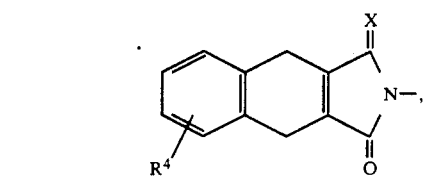
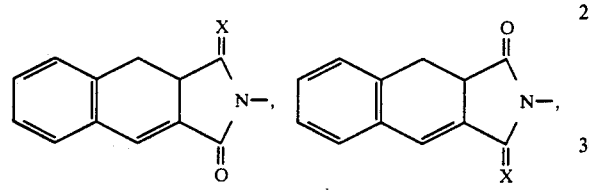
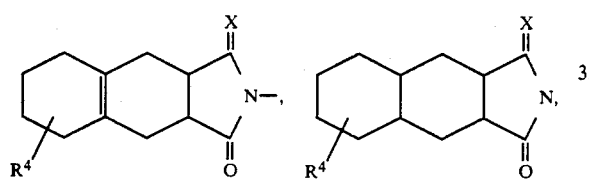
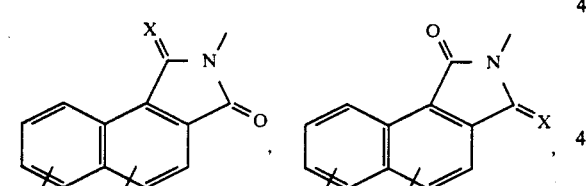
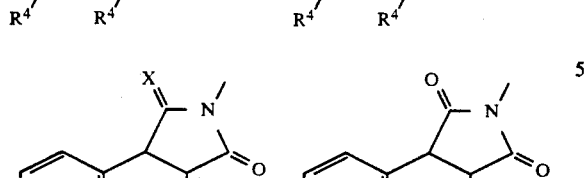
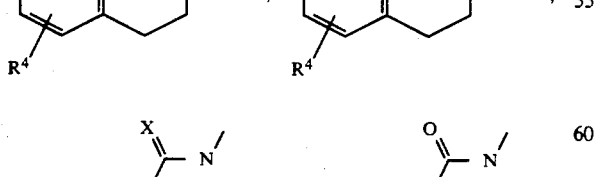
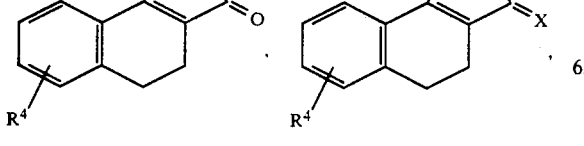
-continued
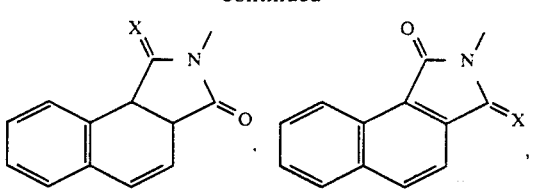
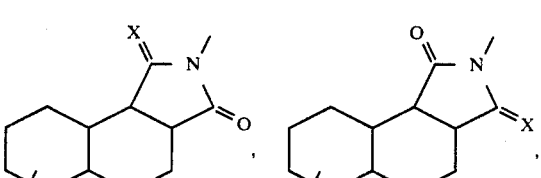
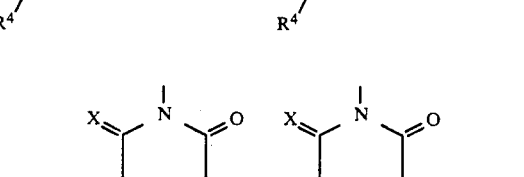
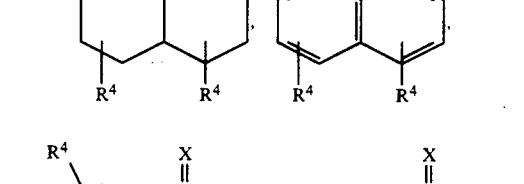
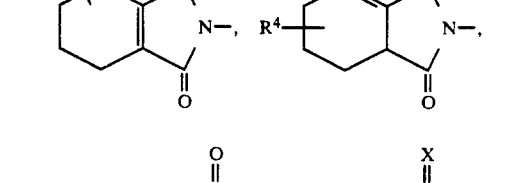
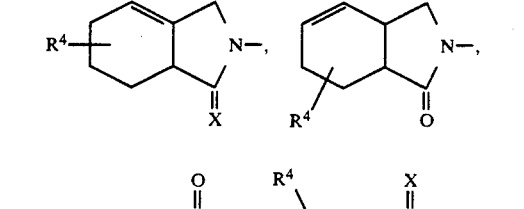
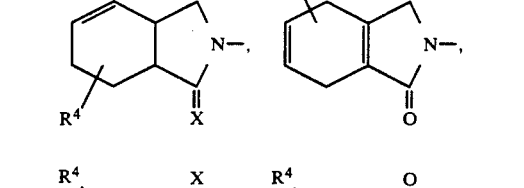
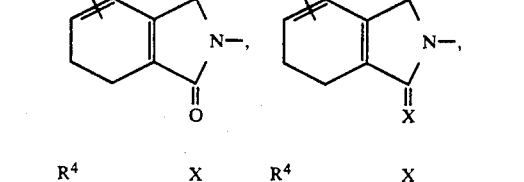
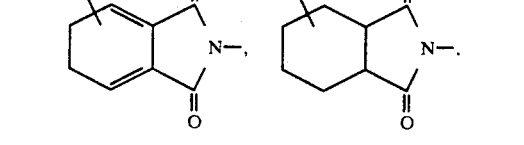

-continued

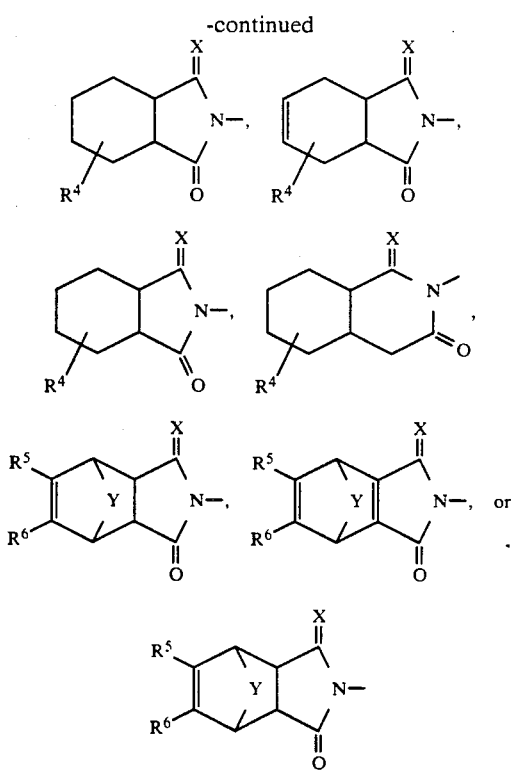

R³ is cycloalkyl of 3 to 8 carbon atoms;
R⁴ is 1-4 substituents independently selected from the group consisting of H, halogen, NO₂, NH₂, haloalkyl of 1 to 3 carbon atoms and 1 to 7 halogen atoms, C₁-C₃ alkyl, NHCOR⁷, NHCO-phenyl, OH, OR⁸ and Ar';
R⁵ and R⁶ independently are H, alkyl of 1 to 3 carbon atoms, Ar" or taken together are —CH=CH—CH=CH—;
R⁷ and R⁸ independently are H or alkyl of 1 to 3 carbon atoms;
X is O; H₂; OH; R⁹, OH; Ar'", OH; H, R⁹; or H, OR⁹;
Y is CH₂, CHR¹⁰, C(R¹⁰)₂, O, CH₂CH₂, (CH₂)₃,

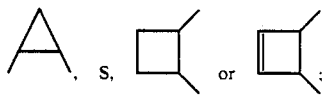

Ar, Ar', Ar" and Ar'" independently are phenyl optionally substituted with 1-5 substituents independently selected from the group consisting of: H, halogen, OH, alkoxy of 1 to 3 carbon atoms, NR¹¹R¹², SH, S(O)ₜR¹³, where t is 0-2, haloalkyl of 1 to 3 carbon atoms and 1 to 7 halogen atoms, alkyl of 1 to 3 carbon atoms, CO₂H, carboalkoxy of 2 to 6 carbon atoms, CN, NO₂, SO₂NH₂, SO₃H, CO₂NR¹⁴R¹⁵, naphthyl, pyridyl, pyrimidyl, quinolyl or isoquinolyl;
R⁹ and R¹⁰ independently are alkyl of 1 to 3 carbon atoms;
R¹¹-R¹⁵ independently are H or alkyl of 1 to 3 carbon atoms;
R¹⁶ is H; OH; O-alkyl of 1-6 carbons; O-acyl of 1-8 carbons; alkyl of 1-12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1-12 carbons; aryl 6-12 carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1-12 carbons; aryl 6-12 carbons); 2- and 3-pyrrolyl; 2- and 3- furyl; 2- and 3- thienyl; 2,3, and 4-pyridyl; 2- and 3-benzolfuryl; 2- and 3- indolyl; 2- and 3-benzothienyl; 2, 3, and 4- quinolyl; and 1, 3, and 4-isoquinolyl;
with the following provisos:
(1) when R¹ is (CH₂)ₚAr (where p is 1); R² is

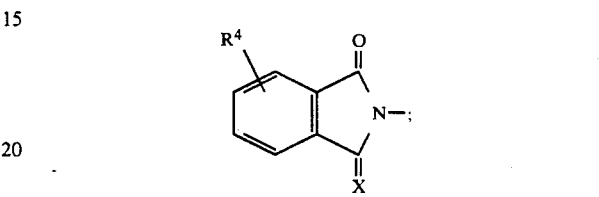

and (CH₂)ₙR², (n=O), is attached at the C-4 position on the piperidine ring; then X cannot be H₂ or O.
(2) R¹⁶ is H, OH, alkyl or aryl when (CH₂)ₙ R² is attached to the 4-position of the piperidine ring.

Some compounds useful in the present invention can exist as optical isomers and both the racemic mixtures of these isomers as well as the individual optical isomers which confer activity are within the scope of compounds useful in the present invention.

In addition some compounds useful in the present invention can exist as cis or trans isomers and although these are not all specifically set forth, the cis and trans fused compounds as known to those skilled in the art, are within the scope of this invention. The selective sigma receptor antagonist compounds useful in the present invention also include cycloalkylpiperidines of the formula:

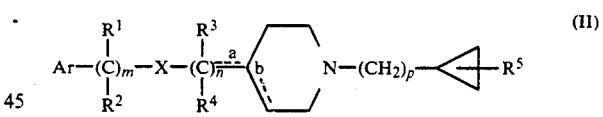

or a pharmaceutically acceptable salt thereof, wherein:
m is 0 to 3;
n is 0 to 3;
provided that m and n are not both O;
p is 0 to 3;
X is O, S, SO, SO₂, NR⁶, CR⁷R⁸,

or CHOH;
R¹, R³ and R⁷ independently are H, alkyl of 1 to 5 carbon atoms, halogen, NR¹⁰R¹¹, OH, CO₂H, carboalkoxy of 2 to 6 carbon atoms, CN, Ar¹, alkoxy of 1 to 5 carbon atoms or alkylthio of 1 to 5 carbon atoms;
R², R⁴ and R⁸ independently are H, alkyl of 1 to 5 carbon atoms, carboalkoxy of 2 to 6 carbon atoms, CN, alkoxy of 1 to 5 carbon atoms or Ar¹;
provided that R¹, R², R³ and R⁴ are not alkoxy of 1 to 5 carbon atoms, alkylthio of 1 to 5 carbon atoms, NR¹⁰R¹¹ or OH when X is O, S, SO, SO₂ or NR⁶;

$R^5$ is H, alkyl, halogen, OH or alkenyl;

$R^6$ is H, alkyl of 1 to 5 carbon atoms or $Ar^1$;

Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$ alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;

$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and a or b is a double bond or a single bond, provided that both are not double bonds.

Preferred compounds useful in the present invention include those compounds of Formula (II) wherein:

X is C(O), CHOH or O;

m is 0;

n and p are 1;

$R^3$–$R^5$ are H; and/or

Ar is phenyl optionally substituted with halogen, $OCH_3$, $NH_2$, $NO_2$ or another phenyl group.

Pharmaceutical compositions comprising an effective amount of a compound of formula (I) or (II) and a pharmaceutically acceptable carrier are useful in the method of the present invention.

Other sigma receptor antagonists lacking or having relatively weak dopamine receptor-blocking activity and expected to be useful in the method of the invention include the compounds claimed in copending, commonly assigned U.S. patent application Ser. No. 07/506,961, filed Mar. 28, 1990 and Ser. No. 07/500,573, filed Mar. 28, 1990, the disclosures of which are hereby incorporated by reference.

DETAILED DESCRIPTION OF THE INVENTION

Figure 1:
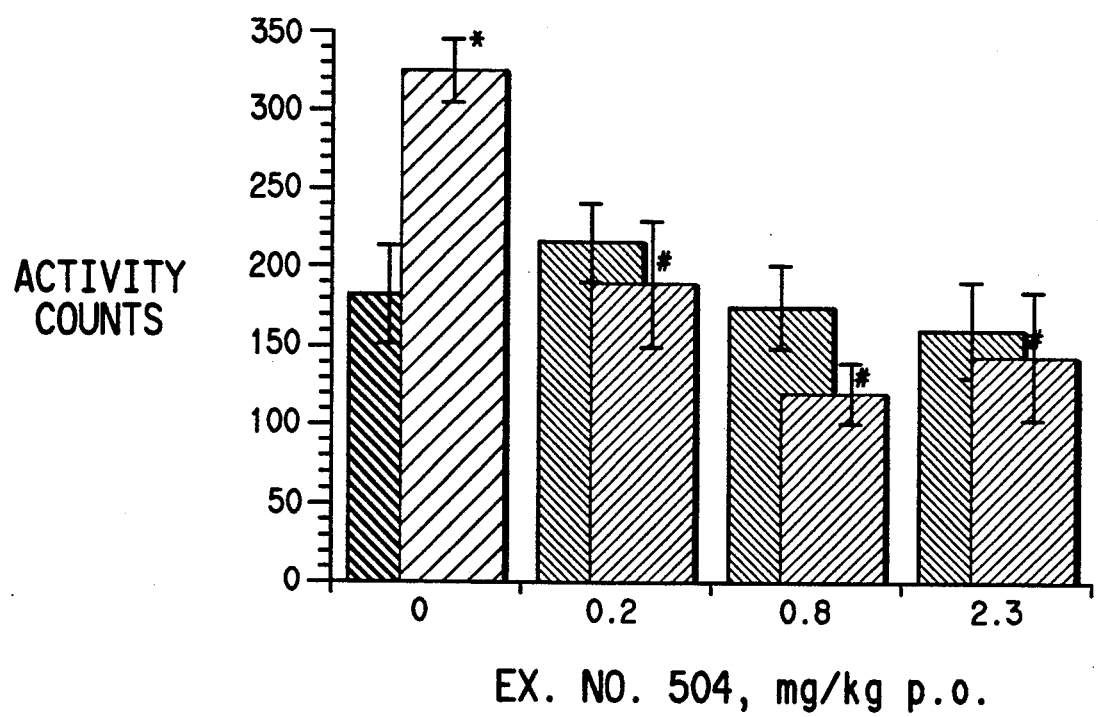
FIG. 1 shows the effect of Ex. No. 504 and D-amphetamine on confinement motor activity in mice. The same data is also shown in table format in Table 3.

We have discovered that sigma receptor antagonists lacking or having relatively weak dopamine receptor blocking activity are useful to reduce and counteract the pharmacological effects of amphetamine in a mammal. We have found that agents which block sigma receptors are able to selectively ameliorate or inhibit amphetamine-induced increases in motor activity, without inhibiting baseline motor activity (i.e., motor activity in the absence of amphetamine).

The sigma receptor antagonists useful in the present invention have weak affinity for dopamine receptors relative to their affinity for sigma receptors. We have discovered that such selective sigma receptor antagonists are able to selectively antagonize the effects of amphetamine in an animal. In mouse animal models, it was found that a representative sigma receptor antagonist having weak dopamine receptor-blocking activity selectively antagonized the amphetamine-induced behavior (amphetamine-increased motor activity) without any significant depression in the normal baseline motor activity in animals in the absence of amphetamine. This important and unexpected finding suggests that sigma receptor antagonists having weak dopamine receptor-blocking activity will effectively antagonize and attenuate the pharmacological effects of amphetamine in humans at doses which will not have significant undesirable neurotoxic or adverse neurological effects.

The selective antagonism and attenuation of the pharmacological effects of amphetamine by sigma receptor antagonists having weak dopamine receptor-blocking activity contrasts with the effect of dopamine receptor-blocking neuroleptics, such as haloperidol or cinuperone. Haloperidol causes an adverse non-selective attenuation of normal motor activity in amphetamine-free animals at the same concentrations required to inhibit amphetamine-induced motor activity. Thus, the sigma receptor antagonists having weak dopamine receptor-blocking activity show a substantial and unexpected advantage over dopamine receptor-blocking neuroleptics in the treatment of amphetamine abuse.

The sigma receptor antagonist compounds useful in this invention include (N-phthalimidoalkyl) piperidines of the formula:

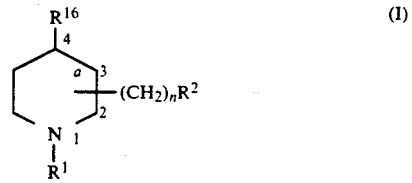

or a pharmaceutically acceptable salt or an N-oxide thereof wherein:

a is a single or double bond, provided that when a is a double bond then $R^2(CH_2)_n$ is attached at C-4;

n is 0–4, provided that when $(CH_2)_nR^2$ is attached to the 2-position of the piperidine ring then n is 2–4;

$R^1$ is $(CH_2)_mR^3$ or $(CH_2)_pAr$, where m is 1–4 and p is 1–4;

$R^2$ is

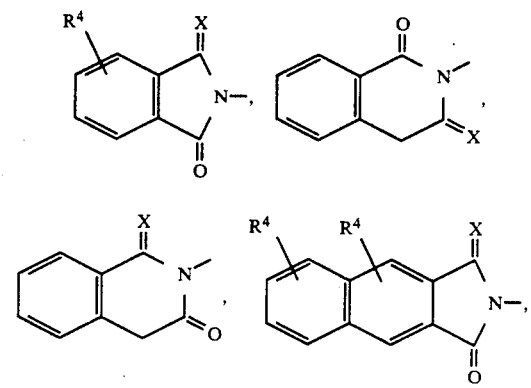

-continued
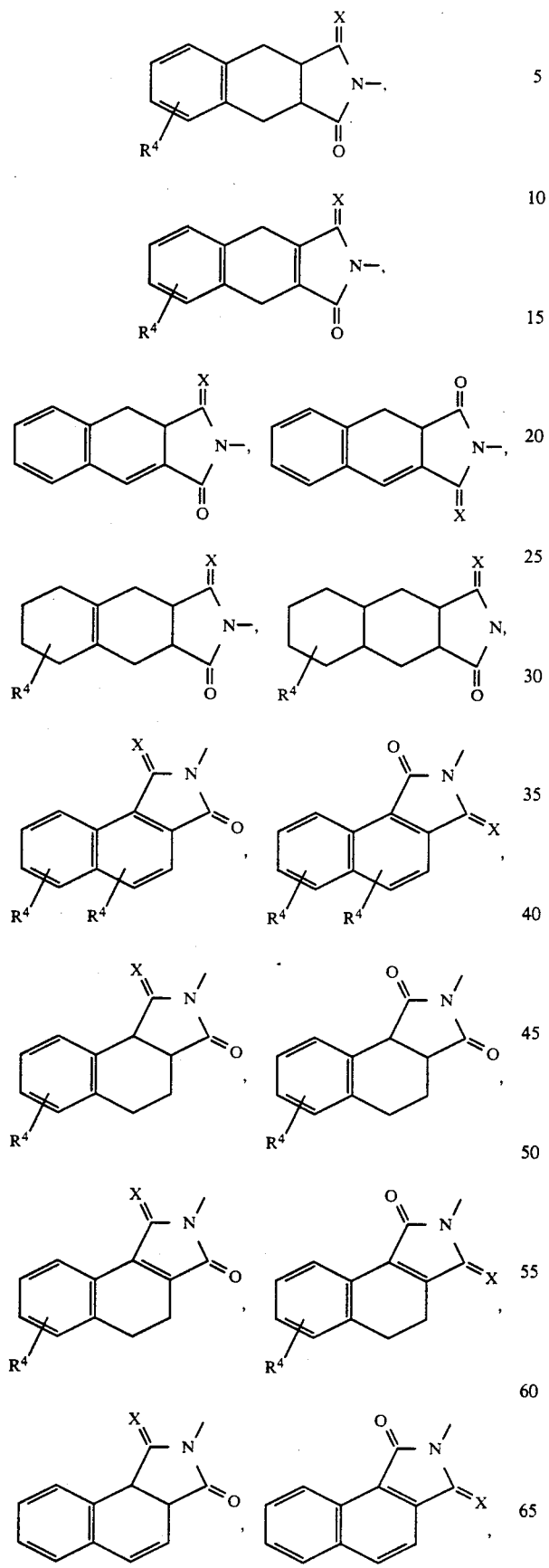
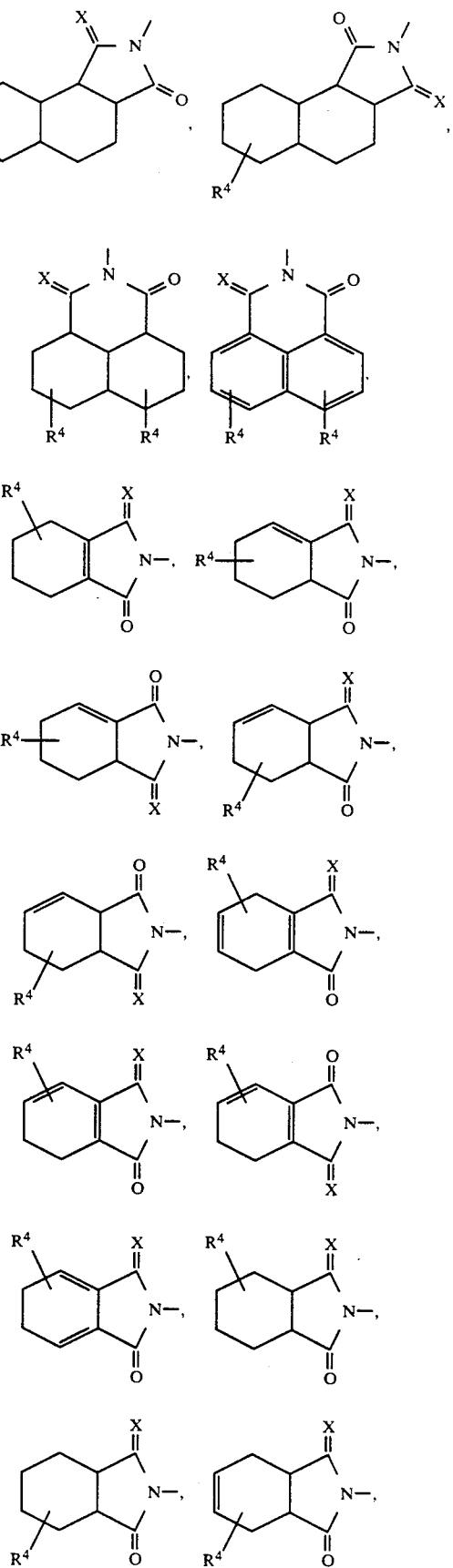

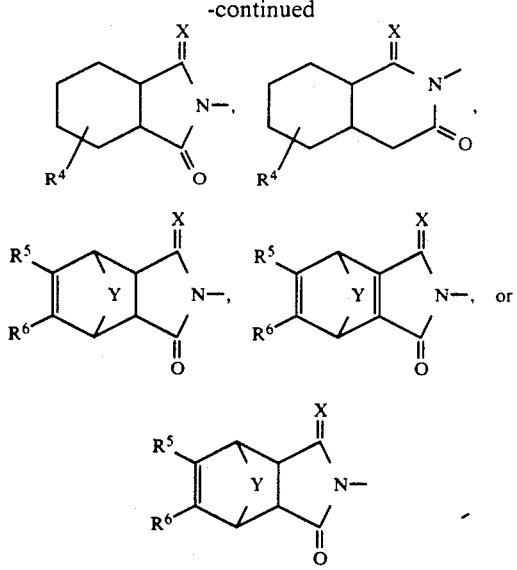

R³ is cycloalkyl of 3 to 8 carbon atoms;
R⁴ is 1–4 substituents independently selected from the group consisting of H, halogen, NO₂, NH₂, haloalkyl of 1 to 3 carbon atoms an 1 to 7 halogen atoms, C₁–C₃ alkyl NHCOR⁷, NHCO-phenyl, OH, OR⁸ and Ar';

R⁵ and R⁶ independently are H, alkyl of 1 to 3 carbon atoms, Ar" or taken together are —CH=CH—CH=CH—;

R⁷ and R⁸ independently are H or alkyl of 1 to 3 carbon atoms;

X is O, H₂; H, OH; R⁹, OH; Ar''', OH; H, R⁹; or H, OR⁹;

Y is CH₂, CHR¹⁰, C(R¹⁰)₂, O, CH₂CH₂, (CH₂)₃,

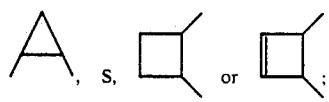

Ar, Ar', Ar" and Ar''' independently are phenyl optionally substituted with 1–5 substituents independently selected from the group consisting of: H, halogen, OH, alkoxy of 1 to 3 carbon atoms, NR¹¹R¹², SH, S(O)ₜR¹³, where t is 0–2, haloalkyl of 1 to 3 carbon atoms and 1 to 7 halogen atoms, alkyl of 1 to 3 carbon atoms, CO₂H, carboalkoxy of 2 to 6 carbon atoms, CN, NO₂, SO₂NH₂, SO₃H, CO₂NR¹⁴R¹⁵, naphthyl, pyridyl, pyrimidyl, quinolyl or isoquinolyl;

R⁹ and R¹⁰ independently are alkyl of 1 to 3 carbon atoms;

R¹¹–R¹⁵ independently are H or alkyl of 1 to 3 carbon atoms;

R¹⁶ is H; OH; O-alkyl of 1–6 carbons; O-acyl of 1–8 carbons; alkyl of 1–12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl 6–12 carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl 6–12 carbons); 2- and 3-pyrrolyl; 2- and 3- furyl; 2- and 3- thienyl; 2,3, and 4-pyridyl; 2- and 3-benzolfuryl; 2- and 3- indolyl; 2- and 3-benzothienyl; 2, 3, and 4- quinolyl; and 1, 3, and 4-isoquinolyl;

with the following provisos:
(1) when R¹ is (CH₂)ₚAr (where p is 1);
R² is

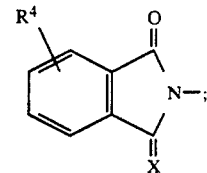

and (CH₂)ₙR², (n=O), is attached at the C-4 position on the piperidine ring; then X cannot be H₂ or O.
(2) R¹⁶ is H, OH, alkyl or aryl when (CH₂)ₙ R² is attached to the 4-position of the piperidine ring.

Preferred compounds useful in the method of the present invention are compounds of Formula (I) for which one or more of the following occur:
n is 1–4;
R¹ is (CH₂)ₚAr;
p is 1–2;
R² is

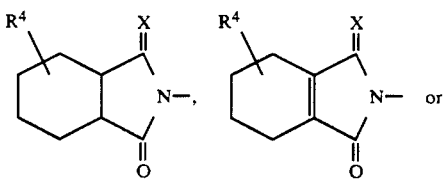

(CH₂)ₙR² is attached at the C-4 position of the piperidine ring;
X is O or H₂;
R⁴, R⁵ and R⁶ are all H,
Ar is phenyl; or
Y is (CH₂)₃ or O.

More preferred compounds useful in the present invention are the compounds of formula (I) wherein n is 1.

Specifically preferred compounds useful in the present invention are compounds of formula (I) wherein:
(1) (CH₂)ₙR² is attached at the C-4 position of the piperidine ring;
n is 1;
R² is

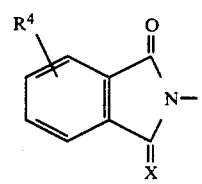

X is O;
R⁴ is H;
R¹ is (CH₂)$_p$Ar;
p is 2; and
Ar is phenyl.
(2) (CH₂)$_n$R² is attached at the C-4 position of the piperidine ring;
n is 1;
R² is

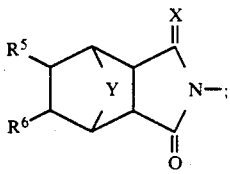

X is O;
Y is (CH₂)₃ and R⁵ and R⁶ are H;
R¹ is (CH₂)$_p$Ar;
p is 2; and
Ar is phenyl.
(3) (CH₂)$_n$R² is attached at the C-4 position of the piperidine ring;
n is 1;
R² is

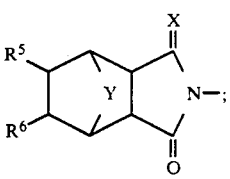

X is O;
Y is O;
R⁵ and R⁶ are H;
R¹ is (CH₂)$_p$Ar;
p is 2; and
Ar is phenyl.
(4) (CH₂)$_n$R² is attached at the C-4 position of the piperidine ring;
n is 1;
R² is

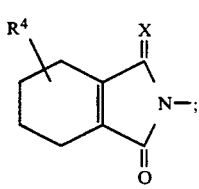

X is H₂;
R⁴ is H;
R¹ is (CH₂)$_p$Ar;
p is 2; and
Ar is phenyl.

The selective sigma receptor antagonist compounds useful in the present invention also include cycloalkyl-piperidines of the formula:

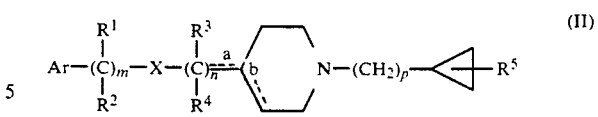

or a pharmaceutically acceptable salt thereof, wherein:
m is 0 to 3;
n is 0 to 3;
provided that m and n are not both O;
p is 0 to 3;
X is O, S, SO, SO₂, NR⁶, CR⁷R⁸,

or CHOH;
R¹, R³ and R⁷ independently are H, alkyl of 1 to 5 carbon atoms, halogen, NR¹⁰R¹¹, OH, CO₂H, carboalkoxy of 2 to 6 carbon atoms, CN, Ar¹, alkoxy of 1 to 5 carbon atoms or alkylthio of 1 to 5 carbon atoms;
R², R⁴ and R⁸ independently are H, alkyl of 1 to 5 carbon atoms, carboalkoxy of 2 to 6 carbon atoms, CN, alkoxy of 1 to 5 carbon atoms or Ar¹;
provided that R¹, R², R³ and R⁴ are not alkoxy of 1 to 5 carbon atoms, alkylthio of 1 to 5 carbon atoms, NR¹⁰R¹¹ or OH when X is O, S, SO, SO₂ or NR⁶;
R⁵ is H, alkyl, halogen, OH or alkenyl;
R⁶ is H, alkyl of 1 to 5 carbon atoms or Ar¹;
Ar and Ar¹ independently are naphthyl, pyridyl, pyrimidyl, indolyl, quinoinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, S(O)$_t$ alkyl of 1 to 3 carbon atoms, where t is 1, 2 or 3, dialkylamino of 2 to 6 carbon atoms, halogen, OH, alkylamino of 1 to 3 carbon atoms, NH₂, CN, NO₂, SO₃H, tetrazole, CO₂H, carboalkoxy of 2 to 6 carbon atoms, CONH₂, SO₂NH₂, COR⁹, CONR¹²R¹³, SO₂NR¹²R¹³, Ar², OAr² or SAr²;
Ar² is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;
R⁹, R¹⁰, R¹¹, R¹² and R¹³ independently are H, alkyl of 1 to 5 carbon atoms or phenyl or R¹⁰ and R¹¹ taken together are an alkylene chain of 3 to 6 carbon atoms or R¹² and R¹³ taken together are an alkylene chain of 3 to 6 carbon atoms; and
a or b is a double bond or a single bond, provided that both are not double bonds.

Preferred compounds useful in the present invention include those compounds of Formula (II) wherein:
X is C(O), CHOH or O;
m is 0;
n and p are 1;
R³-R⁵ are H; and/or
Ar is phenyl optionally substituted with halogen, OCH₃, NH₂, NO₂ or another phenyl group.
Specifically preferred compounds useful in the present invention are:
(a) 1-(cyclopropylmethyl)-4-(2'-(4''-fluorophenyl)-2'-oxoethyl) piperidine
(b) 1-(cyclopropylmethyl)-4-(2'-(4''-fluorophenyl)-2'-oxoethyl) piperidine, hydrobromide salt (c) 1-(cyclopropylmethyl)-4-(2'-(4''-chlorophenyl)-2'-oxoethyl) piperidine (d) 1-(cyclopropylmethyl)-4-(2'-(4''-chlorophenyl)-2'-oxoethyl) piperidine, hydrobromide salt (e) 1-(cyclopropylmethyl)-4-(4'-fluorophenoxymethyl)-piperidine (f) 1-(cyclopropylmethyl)-4-(4'-fluorophenoxymethyl)-piperidine, hydrochloride salt (g) 1-(cyclopropylmethyl)-4-(4'-chlorophenoxymethyl)piperidine (h) 1-(cyclopropylmethyl)-4-(4'-chlorophenoxymethyl)piperidine, hydrochloride salt (i) 1-(cyclopropylmethyl)-4-(4'-nitrophenoxymethyl)-piperidine (j) 1-(cyclopropylmethyl)-4-(2'-(4''-biphenyl)-2'-oxoethyl)piperidine (k) 1-(cyclopropylmethyl)-4-(2'-(4''-biphenyl)-2'-oxoethyl)piperidine, hydrobromide salt.

The preparation of the (N-phthalimidoalkyl) piperidine compounds of Formula I is described in copending, commonly assigned U.S. patent application Ser. No. 07/570,199, filed Aug. 20, 1990, the disclosure of which is hereby incorporated by reference. The compound referred to herein as Ex. No. 504 is designated as the compound of Example Number 504 in U.S. Ser. No. 07/570,199.

The preparation of the 1-cycloalkyl piperidine compounds of Formula II is described in copending, commonly assigned U.S. patent application Ser. No. 07/602,024, filed Oct. 23, 1990, the disclosure of which is hereby incorporated by reference. The compound referred to herein as Ex. No. 3 is referred to as Example Number 3 in U.S. Ser. No. 07/428,097.

Other sigma receptor antagonists lacking or having relatively weak dopamine receptor-blocking activity and expected to be useful in the method of the invention include the compounds claimed in copending, commonly assigned U.S. patent application Ser. No. 07/506,961, filed Mar. 28, 1990 and U.S. Ser. No. 07/500,573, filed Mar. 28, 1990, the disclosures of which are hereby incorporated by reference.

EXAMPLE 1

D-amphetamine was administered to mice and its effect in stimulating motor activity was quantified. The D-amphetamine-stimulated motor activity was used to evaluate the effects of the sigma receptor antagonist in reducing this enhanced motor stimulation; i.e., counteracting the pharmacological effect of amphetamine in the animal.

A representative sigma receptor antagonist of Formula I, Ex. No. 504 reduced the D-amphetamine-stimulated increases in motor activity in mice (Table 1 & FIG. 1). Moreover, Ex. No. 504 was effective at doses which were not depressant on the baseline motor activity in animals not administered with D-amphetamine (i.e., in control saline treated animals) (Table 1 & FIG. 1).

TABLE 1

Effect of Ex. No. 504 and D-Amphetamine on Confinement Motor Activity in Mice

| Treatment | | Methocel | [Ex. No. 505] (mg/kg, po) | | |
|---|---|---|---|---|---|
| | | | 0.2 | 0.8 | 2.3 |
| +Saline, i.p. | N | 8 | 8 | 8 | 8 |
| | Mean | 181 | 215 | 176 | 163 |
| | SEM | 32 | 23 | 26 | 26 |
| +D-Ampheta- | N | 8 | 8 | 6 | 8 |

TABLE 1-continued

Effect of Ex. No. 504 and D-Amphetamine on Confinement Motor Activity in Mice

| Treatment | | Methocel | [Ex. No. 505] (mg/kg, po) | | |
|---|---|---|---|---|---|
| | | | 0.2 | 0.8 | 2.3 |
| mine.SO$_4$, 3.0 mg/kg i.p. | Mean | 326* | 187# | 121# | 146# |
| | SEM | 20 | 73 | 23 | 36 |

Animals were administerd with Ex. No. 504 at 15 min prior to cocaine administration and the start of a 60 min recording session. Data was analyzed by ANOVA and Dunnett's T Test.
*: $p < .05$ from methocel control;
: $p < .05$ from cocaine control.

In contrast, in the same animal model, the neuroleptic haloperidol, which antagonizes both sigma and dopamine receptors, was non-selective in inhibiting motor activity behavior and strongly inhibited baseline motor activity in the absence of amphetamine.

These findings indicate that Ex. No. 504 and other sigma receptor antagonists of Formula I and II may be useful as improved selective medications for amphetamine and amphetamine-related drug abuse problems and other situations where attenuation of the effects of amphetamine with minimum adverse neurological effects would be of medical or social benefit.

Animals

Male CF-1 mice weighing 20–22 grams and CDF rats weighing 200 to 250 grams (Charles River Breeding Laboratories, Kingston, N.Y.) were used. Mice were housed 12 and rats 2 per clear plastic cage (47L×26W×16H cm) with Alpha-Dri bedding, in a temperature regulated room (22° C.), under a normal light-dark cycle, with ad-lib food and water. At least 7 days acclimation to the animal facility was allowed.

Apparatus

Activity was measured in a confined area using 64 isolated plexiglas chambers (9L×8W×31H cm) with an infrared photocell beam 9 cm above the table top. One mouse was placed in each chamber. Each chamber was visually isolated by black plexiglas. Experiments were conducted under normal laboratory illumination. Vertical movement was detected by photocell beam breaks and collected with a Cromemco computer.

Procedure

Mice were fasted overnight brought to the lab and grouped according to treatment approximately 3 hours before injection. Mice were treated with Ex. No. 504 at 15 minutes before treatment with D-amphetamine (3.0 mg/kg, i.p.) after which the animals were placed into the activity chambers. Activity was recorded for 1 hour beginning immediately after D-amphetamine administration.

Dosage Forms

Daily dosage ranges from 1 mg to 2000 mg. Dosage forms (compositions) suitable for administration ordinarily will contain 0.5–95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Co., a standard reference text in this field.

What is claimed is:

1. A method of attenuating the hyperactivity effects of amphetamine or amphetamine-related drugs with pharmacological effects similar to amphetamine in a mammal in need of such attenuating which comprises administering to the mammal an amount effective to reduce the pharmacological effects of the amphetamine or amphetamine-related drug, of a sigma receptor antagonist having the formula:

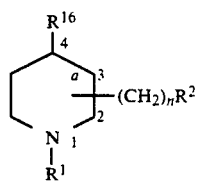

or a pharmaceutically acceptable salt or an N-oxide thereof wherein:

a is a single or double bond, provided that when a is a double bond then $R^2(CH_2)_n$ is attached at C-4;

n is 0-4, provided that when $(CH_2)_nR^2$ is attached to the 2-position of the piperidine ring then n is 2-4;

$R^1$ is $(CH_2)_mR^3$ or $(CH_2)_pAr$, where m is 1-4 and p is 1-4;

$R^2$ is

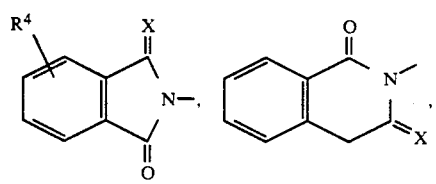

-continued

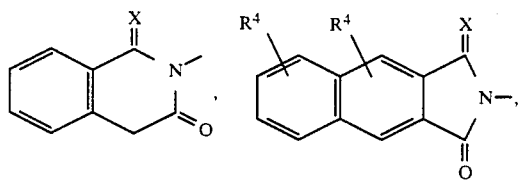

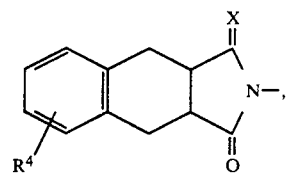

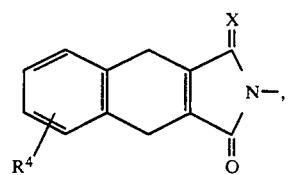

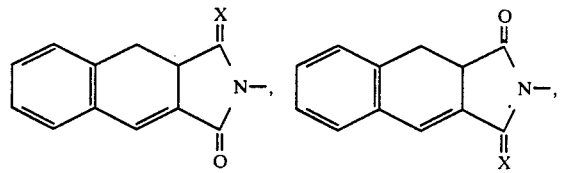

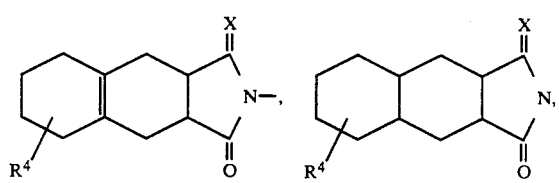

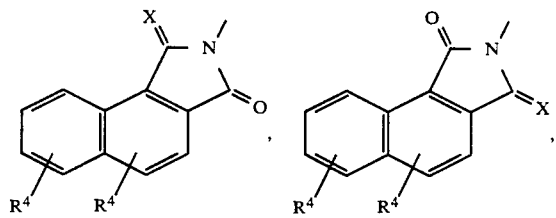

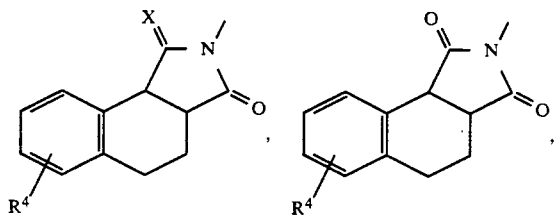

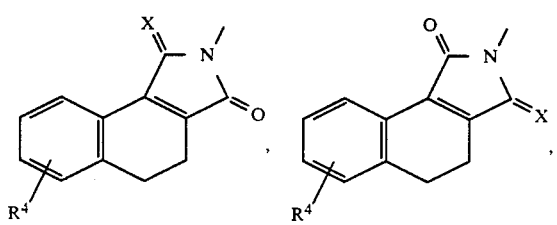

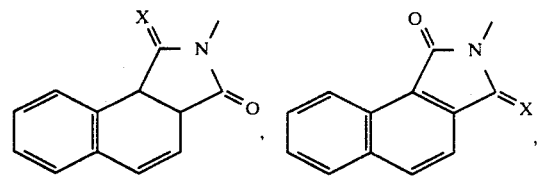
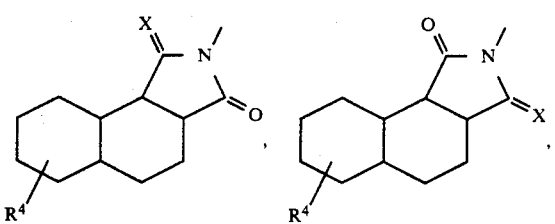
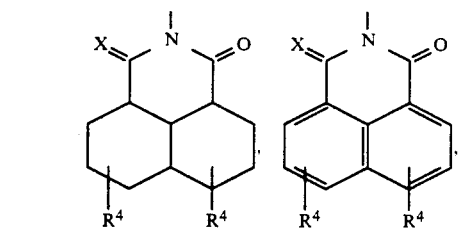
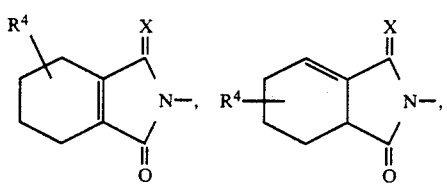
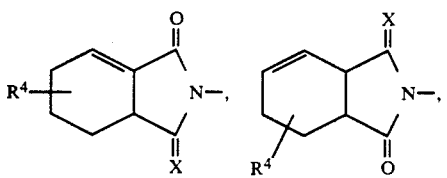
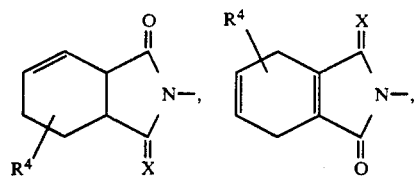
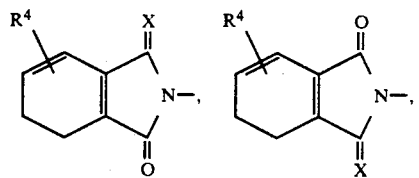
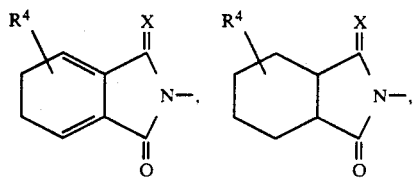

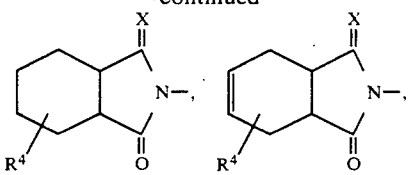
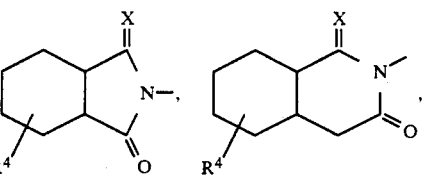
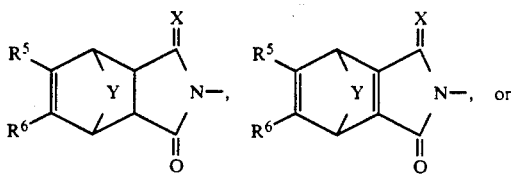
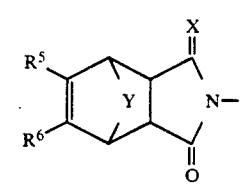

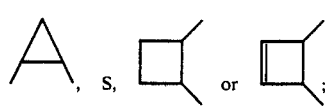

$R^3$ is cycloalkyl of 3 to 8 carbon atoms;

$R^4$ is 1-4 substituents independently selected from the group consisting of H, halogen, $NO_2$, $NH_2$, haloalkyl of 1 to 3 carbon atoms and 1 to 7 halogen atoms, $C_1-C_3$ alkyl, $NHCOR^7$, NHCO-phenyl, OH, $OR^8$ and Ar′;

$R^5$ and $R^6$ independently are H, alkyl of 1 to 3 carbon atoms, Ar″ or taken together are —CH=CH—CH=CH—;

$R^7$ and $R^8$ independently are H or alkyl of 1 to 3 carbon atoms;

X is O; $H_2$; H, OH; $R^9$, OH; Ar‴, OH; H, $R^9$; or H, $OR^9$;

Y is $CH_2$, $CHR^{10}$, $C(R^{10})_2$, O, $CH_2CH_2$, $(CH_2)_3$,

, S, or ;

Ar, Ar′, Ar″ and Ar‴ independently are phenyl optionally substituted with 1-5 substituents independently selected from the group consisting of: H, halogen, OH, alkoxy of 1 to 3 carbon atoms, $NR^{11}R^{12}$, SH, $S(O)_tR^{13}$, where t is 0-2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, naphthyl, pyridyl, pyrimidyl, quinolyl or isoquinolyl;

$R^9$ and $R^{10}$ independently are alkyl of 1 to 3 carbon atoms;

$R^{11}$-$R^{15}$ independently are H or alkyl of 1 to 3 carbon atoms;

$R^{16}$ is H; OH; O-alkyl of 1-6 carbons; O-acyl of 1-8 carbons; alkyl of 1-12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1-12 carbons; aryl 6-12 carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1-12 carbons; aryl 6-12 carbons); 2- and 3-pyrrolyl; 2- and 3- furyl; 2- and 3- thienyl; 2,3, and 4-pyridyl; 2- and 3-benzolfuryl; 2- and 3- indolyl; 2- and 3-benzothienyl; 2, 3, and 4- quinolyl; and 1, 3, and 4-isoquinolyl;

provided however that:

(1) when $R^1$ is $(CH_2)_pAr$ (where p is 1); $R^2$ is

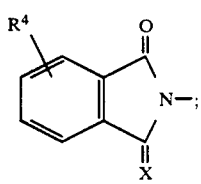

and $(CH_2)_nR^2$, (n=0), is attached at the C-4 position on the piperidine ring; then X cannot be $H_2$ or O, (2) $R^{16}$ is H, OH, alkyl or aryl when $(CH_2)_n R^2$ is attached to the 4-position of the piperidine ring.

2. A method of claim 1 wherein n is 1-4.

3. A method of claim 1 wherein $R^1$ is $(CH_2)_pAr$.

4. A method of claim 1 wherein $R^2$ is selected from the group consisting of

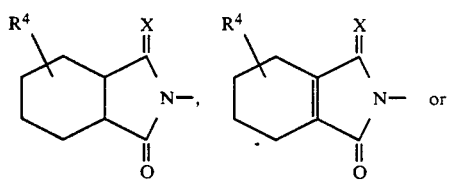

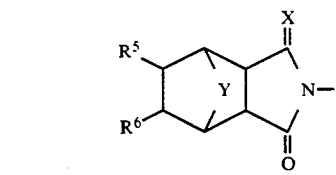

where X, Y, $R^4$, $R^5$ and $R^6$ are as defined in claim 1.

5. A method of claim 1 wherein $(CH_2)_nR^2$ is attached at the C-4 position of the piperidine ring.

6. A method of claim 1 wherein X is O or $H_2$.

7. A method of claim 1 wherein $R^4$, $R^5$ and $R^6$ are all H.

8. A method of claim 1 wherein p is 1 or 2.

9. A method of claim 1 wherein Ar is phenyl.

10. A method of claim 1 wherein Y is $(CH_2)_3$ or O.

11. A method of claim 1 wherein:
n is 1-4;
$R^1$ is $(CH_2)_pAr$;
p is 1-2;
$R^2$ is

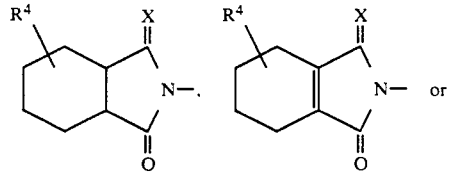

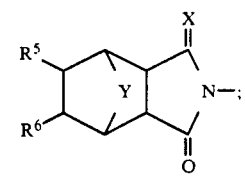

$(CH_2)_nR^2$ is attached at the C-4 position of the piperidine ring; and/or
X is O or $H_2$;
$R^4$, $R^5$ and $R^6$ are all H;
Ar is phenyl,
Y is $(CH_2)_3$ or O.

12. A method of claim 1 wherein:
n is 1;
$R^2$ is

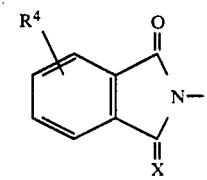

X is O; and
p is 2.

13. A method of claim 1 wherein:
n is 1;
$R^2$ is

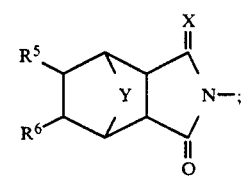

X is O;
Y is $(CH_2)_3$; and
p is 2.

14. A method of claim 1 wherein:
n is 1;
$R^2$ is

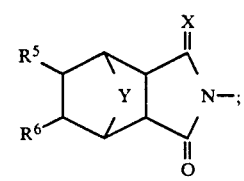

X is O;
Y is O; and
p is 2.

15. A method of claim 1 wherein:
n is 1;

$R^2$ is

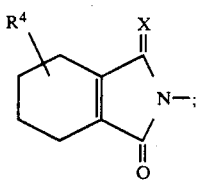

X is $H_2$; and
p is 2.

16. A method of attenuating the effects of amphetamine or amphetamine-related drugs with pharmacological effects similar to amphetamine, in a mammal in need of such attenuating which comprises administering to the mammal an effective amount of a sigma receptor antagonist having the formula:

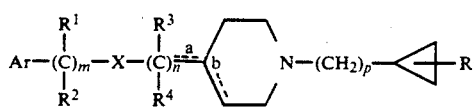

or a pharmaceutically acceptable salt thereof, wherein:
m is 0 to 3;
n is 0 to 3;
provided that m and n are not both 0;
p is 0 to 3;
X is O, S, SO, $SO_2$, $NR^6$, $CR^7R^8$,

or CHOH;
$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;
$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;
provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;
$R^5$ is H, alkyl, halogen, OH or alkenyl;
$R^6$ is H, alkyl of 1 to 5 carbon atoms or $Ar^1$;

Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$ alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;
$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;
$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and
a or b is a double bond or a single bond, provided that both are not double bonds.

17. A method of claim 16 wherein:
X is CO, CHOH or O;
m is 0;
n and p are 1;
$R^3$–$R^5$ are H; and/or
Ar is phenyl optionally substituted with halogen $OCH_3$, $NH_2$, $NO_2$ or another phenyl group.

18. A method according to claim 16 wherein the compound is 1-(cyclopropylmethyl)-4-(2'-(4''-fluorophenyl)-2'-oxoethyl) piperidine.

19. A method according to claim 16 wherein the compound is 1-(cyclopropylmethyl)-4-(2'-(4''-chlorophenyl)-2'-oxoethyl) piperidine.

20. A method according to claim 16 wherein the compound is 1-(cyclopropylmethyl)-4-(4'-fluorophenoxymethyl) piperidine.

21. A method according to claim 16 wherein the compound is 1-(cyclopropylmethyl)-4-(4'-chlorophenoxymethyl)piperidine.

22. A method according to claim 16 wherein the compound is 1-(cyclopropylmethyl)-4-(4'-nitrophenoxymethyl) piperidine.

23. A method according to claim 16 wherein the compound is 1-(cyclopropylmethyl)-4-(2'-(4''-biphenyl)-2'-oxoethyl)piperidine.

* * * * *